United States Patent [19]

Barnes

[11] Patent Number: 5,286,198

[45] Date of Patent: Feb. 15, 1994

[54] DENTURE APPARATUS

[76] Inventor: Larry W. Barnes, 120 N. Mingo Rd., Tulsa, Okla. 74115

[21] Appl. No.: 930,362

[22] Filed: Aug. 17, 1992

[51] Int. Cl.⁵ .................... A61C 13/12; A61C 13/225
[52] U.S. Cl. .................................................. 433/179
[58] Field of Search ................ 433/169, 170, 177, 179

[56] References Cited

U.S. PATENT DOCUMENTS

| | | |
|---|---|---|
| 452,653 | 5/1991 | Stedman . |
| 474,104 | 5/1992 | Stedman . |
| 1,242,989 | 10/1917 | Schreier . |
| 1,322,355 | 11/1919 | Schreier . |
| 1,473,673 | 11/1923 | Elsas . |
| 1,761,902 | 6/1930 | Anderson . |
| 2,252,935 | 8/1941 | Liedberg . |
| 2,309,084 | 1/1943 | Wintrebert . |
| 2,598,998 | 6/1952 | Kaplan . |
| 2,666,988 | 1/1954 | Myers ........................ 433/179 |
| 2,770,881 | 11/1956 | Lodi . |
| 3,043,005 | 7/1962 | Morris . |
| 3,362,072 | 1/1968 | Nowaczyk . |
| 3,495,332 | 2/1970 | Joseph . |

*Primary Examiner*—Gene Mancene
*Assistant Examiner*—Nicholas D. Lucchesi
*Attorney, Agent, or Firm*—Head & Johnson

[57] ABSTRACT

A denture apparatus including a maxillary or upper denture and an opposed mandibular or lower denture. At least one leg extends from the upper denture toward the lower denture so that the leg will engage with the lower denture when the dentures are brought in proximity with each other. A coil spring mechanism for each leg tensions the extending leg in order to urge the lower denture away from the upper denture thereby retaining the dentures in place during eating.

11 Claims, 1 Drawing Sheet

DENTURE APPARATUS

BACKGROUND OF THE INVENTION

The present invention is directed to a denture apparatus for removable dentures. In particular, the present invention is directed to a denture apparatus for removable dentures which will provide a force to urge the lower denture away from the upper denture to assist in retaining the dentures in position during eating. Additionally, the apparatus may be disengaged to eliminate the separation force during other times.

2. Prior Art

In various instances, prosthodontics dentistry calls for the replacement of teeth with removable dentures. This may be called for in various instances including periodontal disease, decay or injury.

Where a full denture is utilized, the base of the upper denture normally covers the palate. The lower denture may be horseshoe-shaped to leave room for the tongue. A full denture is supported by the underlying gum and bone tissues of the dental ridge.

A lower denture is less stable that an upper denture. Moreover, it is known that a full denture can stand only very limited chewing pressure. When a denture wearer is eating with the dentures in place, the lower plate has a tendency to be displaced or flip up when the wearer is biting in the front or on the sides.

At least one estimate is that full dentures can only withstand one-tenth the chewing pressure of natural teeth.

Various provisions have been made in the past to affix or connect the upper denture to the lower denture. Examples of such approaches in Liedberg (U.S. Pat. No. 2,252,935), Anderson (U.S. Pat. No. 1,761,902) and Elsas (U.S. Pat. No. 1,473,673).

Morris (U.S. Pat. No. 3,043,005) discloses a dental anchoring system having a pair of leaf springs affixed to one of the plates to exert an anchoring separation of the plates.

Nothing in the prior art suggests or discloses the use of coil spring mechanisms to tension an extending leg or legs in order to urge the dentures away from each other and assist in retaining proper positioning of the dentures during eating.

Moreover, nothing in the prior art suggests a denture apparatus which will assist in retaining the position of the dentures during eating, yet may be disabled during other periods.

Accordingly, it is a principal object and purpose of the present invention to provide a denture apparatus which will provide a force to retain the position of the dentures during eating yet may be disabled at other times.

SUMMARY OF THE INVENTION

The present invention provides a denture apparatus having an upper and an opposed lower denture. The upper denture and lower denture have corresponding teeth.

The upper denture includes a right molar pad and a left molar pad. Likewise, the lower denture includes a right molar pad and a left molar pad.

A leg extends outward from the upper molar pad toward the lower left molar pad. The leg includes an indented notch at its extreme end.

The leg is tensioned by a coil spring, a portion of which is embedded within the upper left molar pad. When the upper denture and lower denture are brought together, the leg will engage with the lower left molar pad. Accordingly, the leg urges the lower denture away from the upper denture.

An optional wear plate may be provided on the lower left molar pad to prevent wearing of the molar pad to assist in receiving the leg. An optional upstanding lip on the wear plate extends upward toward the upper denture. The upstanding lip acts to prevent movement of the leg past the lip when the mouth is being closed.

A locking post extends from the upper denture and is substantially aligned with the upper denture. A portion of the locking post is embedded within the upper denture. The leg will be moved by the denture wearer and swung radially toward the upper denture. The indented notch ma be engaged with the locking post so that the locking post will reside within the indented notch to retain the leg.

When the denture wearer desires to eat with the dentures in place, the reverse procedure is performed. The indented notch on the leg is disengaged from the post. When this is accomplished, the leg will spring back toward the relaxed position in angular relation to the upper denture. The leg is thus movable between a position aligned with the upper denture and a position extending away from the upper denture and in angular relation therewith.

DETAILED DESCRIPTION OF THE PREFERRED EMBODIMENT

Figure 1:
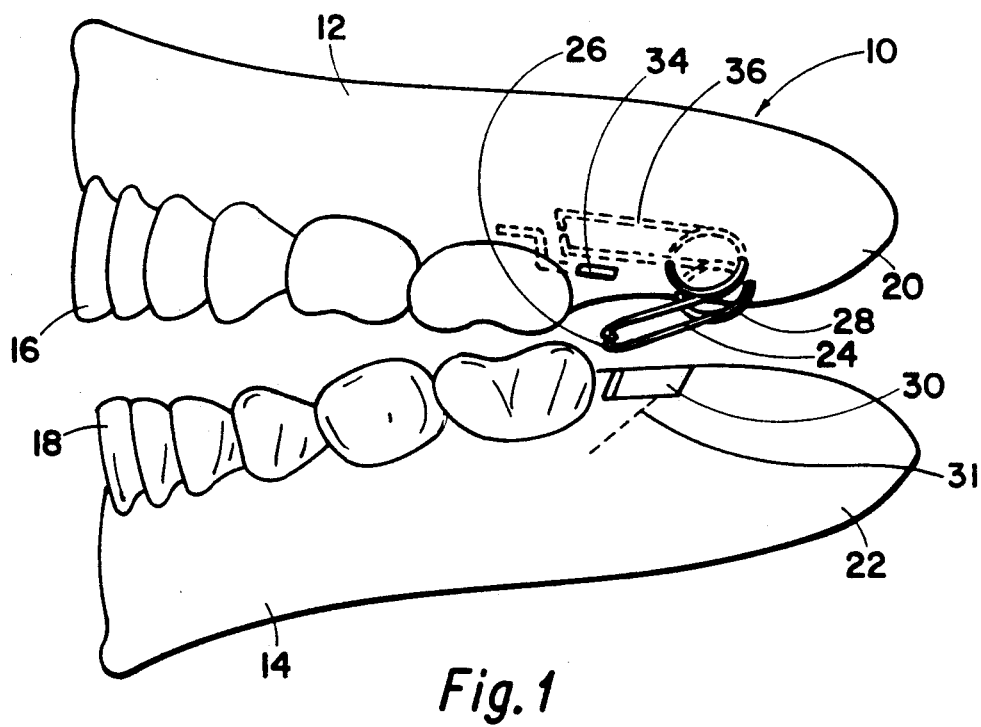
FIG. 1 illustrates a side view of a denture apparatus constructed in accordance with the present invention.

Referring to the drawings in detail, FIG. 1 illustrates a side view of a denture apparatus 10 constructed in accordance with the present invention. The denture apparatus includes a maxillary denture 12 and an opposed mandibular lower denture 14. The upper denture and lower denture have corresponding teeth 16 and 18, respectively.

The upper denture and lower denture are used as replacements for natural teeth and are supported by the underlying gum and bone tissues of the dental ridge of the patient (not shown).

The upper denture 12 and lower denture 14 may take various forms and are well known in the art.

When a denture wearer eats with the front teeth, the upper denture and lower denture are brought together under force. A leverage force is created which may dislodge the positioning of the dentures.

The upper denture includes a right molar pad and a left molar pad 20 behind the last molars (only the upper left molar pad is visible in FIG. 1). The upper molar pads or maxillary tuberosity are posterior to the last permanent molar. Likewise, the lower denture includes a right molar pad and a left molar pad 22 behind the last molars (only the lower left molar pad is visible in FIG. 1). The lower molar pad or mandibular retromolar pad is a recognized anatomical structure which is posterior or distal to the last molar just in front of the ascending ramus of the mandible.

A leg 24 extends outward from the upper left molar pad 20 toward the lower left molar pad 22 and in angular relation therewith. In the present embodiment, the leg 24 is constructed of a loop of wire. The leg 24 includes an indented notch 26 at its extreme end.

The leg 24 is tensioned by utilization of a coil spring 28. A portion of the coil spring 28 is embedded within the upper left molar pad as shown by the dashed lines in FIG. 1. The leg 24 is a part of and extends from the coil spring so that the leg is at all times under tension.

When the upper denture 12 and lower denture 14 are brought together, such as occurs during eating, the leg 24 will engage with the lower left molar pad 22.

The leg will engage with the lower denture prior to the upper and lower teeth being brought together. Accordingly, the leg urges the lower denture 14 away from the upper denture 12. This denture separating force will counteract the force from eating with the front teeth.

The leg is in angular relation to the lower denture 14. Accordingly, as the mouth continues to close after the leg engages the lower denture, the leg will move in response to the lower denture and also slide the leg forward slightly. As the leg slides on the wear plate, the dentures are caused to come into proper occlusion or positioning during the eating function. This minimizes sore spots which are often caused by dentures.

An optional wear plate 30 may be provided on the lower left molar pad 22 to prevent wearing of the molar pad and to assist in receiving the leg. The wear plate has a mesially extending retention rod 31 which is embedded in the base plate to be retained in the investment material with the denture teeth.

An optional, upstanding lip 32 may be provided on the wear plate extending upward toward the upper denture. The upstanding lip 3 acts to prevent movement of the leg past the lip when the mouth is being closed. Accordingly, the lip assists in retaining the dentures from moving out of alignment with each other.

The leg and coil spring 28 of the present invention might extend from the lower denture toward the upper denture, although it has been found that the present arrangement is preferable to avoid in interfering with the tongue.

A locking post 34 extends from the upper denture 12 and is generally aligned with the upper denture. A portion of the locking post 34 is embedded within the upper denture as shown by the dashed lines. At times when the patient is not eating, the leg 24 may be moved out of the way since it is not necessary. In that case, the leg 26 will be moved by the patient and swung radially toward the upper denture.

It will be recalled that the leg is under tension and will not be retained in the position aligned with the upper denture unless held in that position. The indented notch 26 may be engaged with the post, so that the locking post 34 will reside within the indent. This acts to retain the leg out of the denture wearer's way.

When the patient desires to eat with the dentures in place, the reverse procedure is performed. The indented notch in the leg is disengaged from the post 34. This may be easily accomplished with one finger of the denture wearer. Alternatively, a toothpick with an indention or other device might be utilized. When this accomplished, the leg will spring back toward the relaxed position shown in FIG. 1.

It may be seen from the foregoing that the leg 24 is movable between a position aligned with the upper denture and a position extending away from the upper denture and in angular relation therewith.

The foregoing discussion has been relegated to the upper left molar pad and lower left molar pad. It is contemplated that a similar leg and coil spring would be utilized on the upper right molar pad and the lower right molar pad (not seen in FIG. 1).

Figure 2:
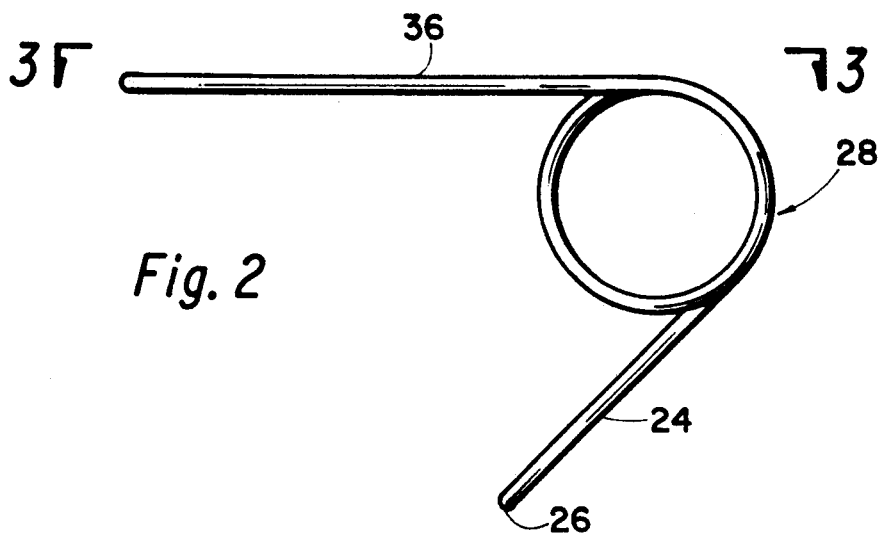
FIG. 2 illustrates a leg and coil spring shown a part from the denture apparatus of the present invention.

FIG. 2 illustrates a side view of the coil spring 28 and leg 24 a part from the upper denture and lower denture. The coil spring 28 includes a stationary leg 36 which is embedded within the upper denture as seen by the dashed lines in FIG. 1.

Figure 3:
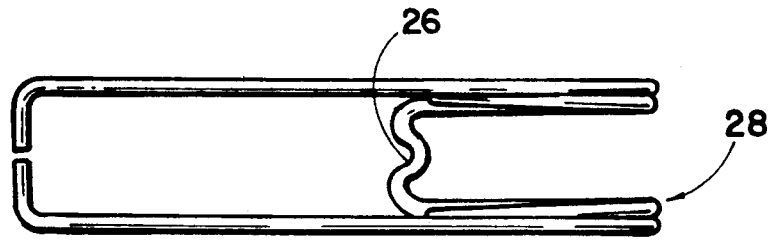
FIG. 3 illustrates a top view of the coil spring and leg shown in FIG. 2.

FIG. 3 illustrates a top view of the coil spring 28 and leg 24 apart from the upper denture 12. The indented notch 26 of the leg 24 may be readily observed. As previously described, the indented notch will mate with the lock down post 34 in order to retain the leg when the patient is not eating.

To produce a denture apparatus in accordance with the present invention, traditional method is modified somewhat. Initially, a wax prototype is fashioned to the shape of the denture wearer's mouth. The wear plate is embedded in the wax prototype. The coil spring is partially embedded in the wax prototype in the maxillary tuberosity area. The lockdown post is embedded in the wax prototype. Thereafter, the remainder of the spring and the lockdown leg are covered with plaster to prevent any movement during the subsequent stages. A plaster mold is then produced using the wax prototype. The plaster is poured around the wax prototype and is allowed to harden. Thereafter, the wax is melted or boiled away so that the plaster mold remains. Finally, the void is packed with acrylic or other material to be used in the final dentures and is allowed to cure. When the plaster surrounding the coil spring and lockdown posts is removed, they will be free and may be used in the manner previously described.

While the discussion herein has been directed to full dentures, it will be understood that the invention may be utilized with partial dentures as well.

Whereas, the present invention has been described in relation to the drawings attached hereto, it should be understood that other and further modifications, apart from those shown or suggested herein, may be made within the spirit and scope of this invention.

What is claimed is:

1. A denture apparatus which comprises:
   (a) an upper denture;
   (b) an opposed lower denture;
   (c) coil at least one spring means; and
   (d) at least one leg extending from said at least one coil spring means, said leg and said coil spring means attached only to said upper denture, said at least one leg adapted to contact said lower denture when said dentures are brought in proximity with each other in order to urge said lower denture away from said upper denture.

2. A denture apparatus as set forth in claim 1 including a wear plate on said lower denture to receive said at least one extending leg when said dentures are brought in proximity with each other.

3. A denture apparatus as set forth in claim 2 including an upstanding lip on said wear plate to prevent movement of said at least one leg past said lip.

4. A denture apparatus as set forth in claim 1 wherein said upper denture includes a right molar pad and a left molar pad and including a pair of said coil spring means and said legs, one leg extending from the right molar pad of said upper denture and the other leg extending from the left molar pad of said upper denture.

5. A denture apparatus as set forth in claim 4 wherein each said coil spring means is partially embedded in said molar pads.

6. A denture apparatus having an upper denture and an opposed lower denture, which apparatus comprises:
   (a) at least one coil spring means;
   (b) at least one leg extending from at least one coil spring means, said at least one leg movable between a position aligned with said upper denture and a position extending away from said upper denture wherein each leg and coil spring means are attached only to said upper denture, allowing contact with said lower denture when said dentures are brought in proximity with each other in order to urge said lower denture away from said upper denture when said dentures are brought in proximity with each other.

7. A denture apparatus as set forth in claim 6 including a wear plate on said lower denture to receive said at least one extending leg when said at least one leg engages said lower denture.

8. A denture apparatus as set forth in claim 6 including an upstanding lip on said wear plate to prevent movement of said at least one leg past said lip.

9. A denture apparatus which comprises:
   (a) an upper denture;
   (b) an opposed lower denture;
   (c) at least one leg extending from said upper denture toward said lower denture, wherein said at least one leg will engage with said lower denture when said dentures are brought in proximity with each other; and
   (d) coil spring means for each leg to tension said each leg in order to urge said lower denture away from said upper denture; and
   (e) a locking post extending from said upper denture to retain said at least one leg when said at least one leg is not in use.

10. A denture apparatus as set forth in claim 9 wherein said at least one leg comprises a loop of wire having an indented notch at its end, and wherein said leg may be moved so that said locking post will reside within said indent to retain said at least one leg.

11. A process to produce a denture apparatus having an upper denture and an opposed lower denture, which process comprises:
   preparing a wax prototype to the shape of the denture wearer;
   partially embedding a coil spring in said wax prototype;
   embedding a wear plate and a lockdown post in said wax prototype;
   preparing a plaster mold using said wax prototype with said coil spring and lockdown post covered with plaster; and
   preparing said dentures from said plaster mold.

* * * * *

UNITED STATES PATENT AND TRADEMARK OFFICE
CERTIFICATE OF CORRECTION

PATENT NO. : 5,286,198
DATED : February 15, 1994
INVENTOR(S) : Larry W. Barnes

It is certified that error appears in the above-indentified patent and that said Letters Patent is hereby corrected as shown below:

Column 2, line 16, "ma" should be --may--.

Column 3, line 33, "3" should be --32--.

Column 4, claim 1, line 4, "coil at least one" should be --at least one coil--.

Column 5, claim 6, line 4, insert --said-- between "from" and "at"

Signed and Sealed this

Twenty-third Day of May, 1995

Attest:

BRUCE LEHMAN

*Attesting Officer*     *Commissioner of Patents and Trademarks*